United States Patent [19]

Duffy et al.

[11] Patent Number: 5,282,466
[45] Date of Patent: Feb. 1, 1994

[54] SYSTEM FOR DISABLING OXIMETER IN PRESENCE OF AMBIENT LIGHT

[75] Inventors: Timothy J. Duffy, Anaheim; Ralph M. Kerns, Laguna Niguel, both of Calif.; James F. Kelley, Coon Rapids; Eric J. Fogt, Maple Grove, both of Minn.

[73] Assignee: Medtronic, Inc., Minneapolis, Minn.

[21] Appl. No.: 770,672

[22] Filed: Oct. 3, 1991

[51] Int. Cl.$^5$ ............................................. A61B 5/00
[52] U.S. Cl. ..................................... 128/633; 128/634
[58] Field of Search ............... 128/633, 634, 664, 665; 356/39-41

[56] References Cited

U.S. PATENT DOCUMENTS

| | | | |
|---|---|---|---|
| 3,647,299 | 3/1972 | Lavallee | 356/41 |
| 4,281,645 | 8/1981 | Jöbsis | 128/633 |
| 4,407,290 | 10/1983 | Wilber | 128/633 |
| 4,444,498 | 4/1984 | Heinemann | 356/246 |
| 4,447,150 | 5/1984 | Heinemann | 356/41 |
| 4,453,218 | 6/1984 | Sperinde et al. | 364/416 |
| 4,523,279 | 6/1985 | Sperinde et al. | 364/416 |
| 4,603,700 | 8/1986 | Nichols et al. | 128/633 |
| 4,651,741 | 3/1987 | Passafaro | 128/633 |
| 4,684,245 | 8/1987 | Goldring | 356/41 |
| 4,714,080 | 12/1987 | Edgar, Jr. et al. | 128/633 |
| 4,714,341 | 12/1987 | Hamaguri et al. | 128/633 |
| 4,744,656 | 5/1988 | Moran et al. | 356/243 |
| 4,745,279 | 5/1988 | Karkar et al. | 250/343 |
| 4,776,340 | 10/1988 | Moran et al. | 128/634 |
| 4,781,195 | 11/1988 | Martin | 128/633 |
| 4,810,090 | 3/1989 | Boucher et al. | 356/39 |
| 4,823,167 | 4/1989 | Manska et al. | 356/243 |
| 4,880,304 | 11/1989 | Jaeb et al. | 356/41 |
| 4,981,355 | 1/1991 | Higgins | 356/243 |
| 5,029,583 | 7/1991 | Meserol et al. | 128/633 |
| 5,069,213 | 12/1991 | Polczynski | 128/633 |
| 5,088,493 | 2/1992 | Giannini et al. | 128/633 |
| 5,111,817 | 5/1992 | Clark et al. | 128/633 |
| 5,113,862 | 5/1992 | Mortazavi | 128/633 |

FOREIGN PATENT DOCUMENTS 0361999  8/1989  European Pat. Off. ........ A61B 5/14

Primary Examiner—Randall L. Green
Assistant Examiner—Gina M. Gaultieri
Attorney, Agent, or Firm—Terry L. Wiles; Harold R. Patton

[57] ABSTRACT

A system for disabling an oximetric device when radiation-carrying channels are exposed to excess ambient radiation is disclosed. It includes a transmitter channel adjacent the sample to be measured, means for isolating the channel from the sample so that it does not carry radiation reflected from or transmitted through the sample, a detector for receiving the transmitted signal, if any, and means for disabling the output in response to the transmitted signal. Preferably, the transmitter channel runs parallel to other transmitter channels in the device, and is isolated from undue ambient light. The system preferably includes means for determining when the second transmitted signal exceeds background noise and the output is disabled when the second transmitted signal exceeds background noise. In general, the sample is a fluid, usually blood, passing through a cuvette adjacent the fiber-optic channels, the cuvette defining an area of radiation absorption adjacent the transmitter channel so that the transmitter does not carry reflected or transmitted radiation from the sample. Also disclosed is a fiber-optic sensor for measuring components of a composition by detecting transmitted or reflected, usually reflected, radiation including such a system, and the cuvette therefore. Finally, a method of disabling the output of an oximetric device when the fiber-optic channels are exposed to undue ambient radiation is disclosed.

9 Claims, 15 Drawing Sheets

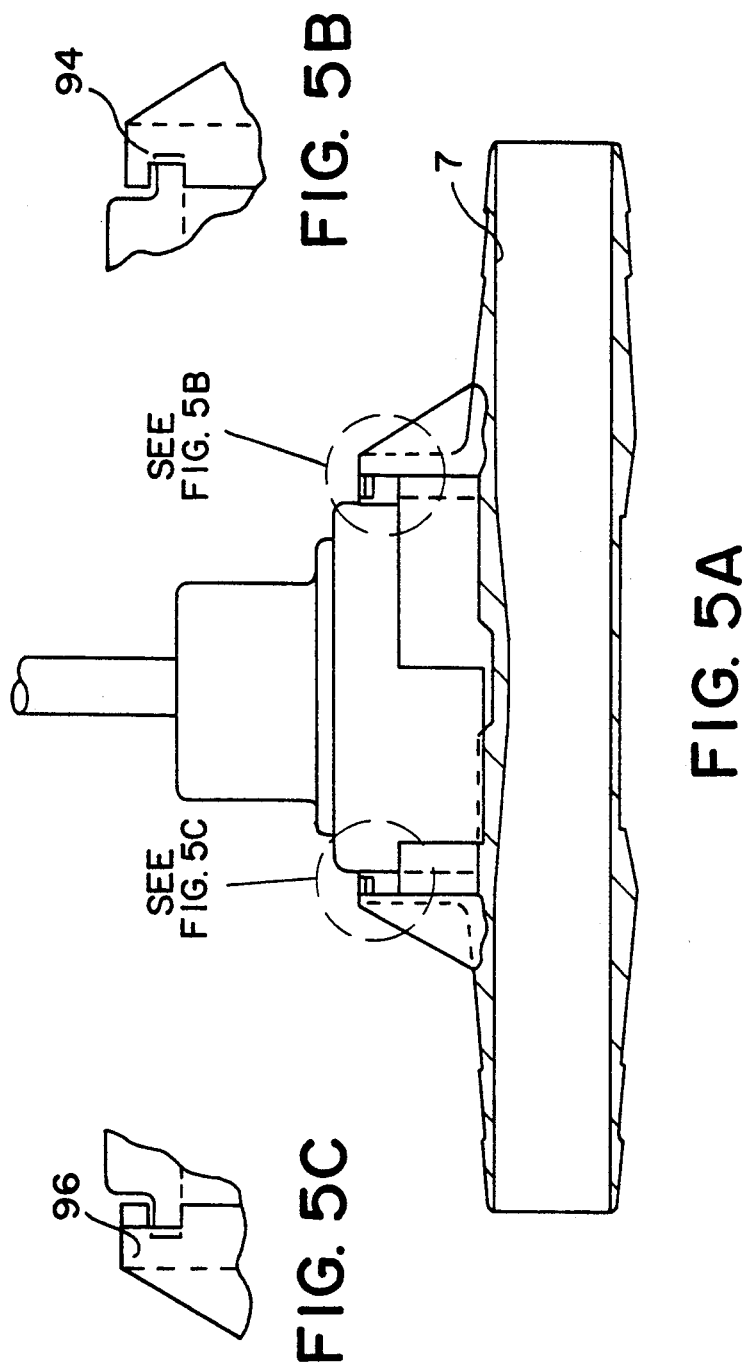

SYSTEM FOR DISABLING OXIMETER IN PRESENCE OF AMBIENT LIGHT

BACKGROUND OF THE INVENTION

1. Field of the Invention

This invention relates to sensors for determining oxygen saturation and hematocrit of the blood as it flows through an extracorporeal blood circuit in which it is oxygenated during bypass surgery and the like.

2. Description of the Prior Art

Fiber-optic sensors for the determination of oxygen saturation (amount of oxygenated hemoglobin) and/or the determination of hematocrit (amount of red blood cells), in the blood in an extracorporeal circuit or otherwise are disclosed in U.S. Pat. Nos. 4,444,498, 4,447,150, 4,651,741, 4,745,279, 4,776,340 and others. Many such sensors function by providing light to the blood sample via a fiber-optic cable, measuring the amount of reflected or transmitted light and calculating oxygen saturation or hematocrit based on those measurements. Light emitting diodes (LEDs) have been used in these devices to provide radiation at given wavelengths to the sample via the fiber-optic input cables; other fiber-optic cables have transmitted the light reflected by or transmitted through the sample at those wavelengths to photodiodes to produce a current proportionate to the reflected or transmitted light. In general, the LEDs alternately, or in series, emit light of one wavelength and then another. See Heinemann, U.S. Pat. No. 4,444,498, Lavallee, U.S. Pat. No. 3,647,299, Goldring, U.S. Pat. No. 4,684,245.

With respect to hematocrit, it has been calculated using a ratio of the amount of light reflected from the blood at two different distances from the light source; the isobestic point for oxygen saturation (about 810 to 820 nm) is the wavelength suggested because it is not influenced by the oxygen saturation level. Two detectors are used to receive the reflected light at two different distances from the source, all as disclosed in Moran, U.S. Pat. No. 4,776,340. In Karkar, U.S. Pat. No. 4,745,279, hematocrit in a blood circuit is measured by diffusion of light downstream from an LED source.

In sensors for oxygen saturation, often called oximeters, oxygen saturation has been determined by using the following ratio with light input at about 665 nm and about 820 nm.

$$\text{Ratio} = R_{820}/R_{665}$$

665 nm is a point of large difference between absorption of deoxyhemoglobin and oxyhemoglobin; 820 nm or thereabouts is the isobestic point at which the absorption is identical for both compounds.

A problem is that ambient light can interfere with the measurement to produce misleading results when there is a break in the cable or when the cable or the instrument is disconnected. Oxygen saturation and hematocrit readings will still be displayed, but are erroneously based on the amount of ambient radiation coming down the cable. In Karkar, U.S. Pat. No. 4,745,279, mentioned above, the hematocrit measurement is corrected by data received from a compensation sensor not exposed to the blood. The compensation sensor is connected in series with the hematocrit sensor and the ratio of their readings taken to produce a signal for the raw hematocrit measurement, to compensate for problems arising from temperature, optical noise, drive current, and aging of the light-emitting diodes.

In Nichols, et al., U.S. Pat. No. 4,603,700, a monitoring circuit is disclosed which reads the voltage at the detector (after exposure to the sample) and digitizes it. When the voltage is unexpected (for example, due to a disconnected probe), an appropriate error message is displayed such as "no probe" and the program is restarted.

Heinemann, U.S. Pat. Nos. 4,444,498 and 4,447,150, discloses a system in which a switch creates a pull-up resistor to give grossly, and obviously erroneous, reading, until a cuvette which has been inadvertently detached is reattached.

Sperinde, et al., U.S. Pat. No. 4,523,279, discloses an oximeter catheter apparatus which measures the reflected intensity of the wavelength of interest and compares it to previously-stored and continually revised intensity levels, to minimize the effect of momentarily high radiation pulses due to changes of catheter position in the blood vessel.

Sperinde, et al., U.S. Pat. No. 4,453,218, discloses a signal filter method and apparatus in which a separate light source is added. The reflected reading from that source is used to calibrate and continually correct a baseline signal which is then used to create a maximum signal level. Where the incoming readings from the regular light source are higher than the maximum signal level, the system does not read them in order to avoid erroneously high readings.

This description of art is not intended to constitute an admission that any patent, publication or other information referred to is "prior art" with respect to this invention, unless specifically designated as such. In addition, this section should not be construed to mean that a search has been made or that no other pertinent information as defined in 37 C.F.R. § 1.56(a) exists.

A problem with some of the above devices is that accurate but unexpectedly high signals may, in fact, be discarded by the correction mechanism. In other devices, high signals may be thought to be accurate rather than indicative of a problem. Some of the devices require the addition of an additional light source and others require the inclusion of complex monitoring and calculating functions in the device, or at least in the software, in order to function. Some are designed particularly for use with catheters and are not appropriate for use with oximeter devices adapted to extracorporeal blood circuits. It would, thus, be desirable to provide a device which eliminates some of these difficulties.

SUMMARY OF THE INVENTION

In one aspect, the present invention is a means for eliminating erroneous readings in a fiber-optic sensor by disabling the device upon entry of ambient light into the system.

In this aspect, the system for disabling the device includes an isolated transmitter channel extending from the sample to a detector, and means for isolating the transmitter channel from the sample so that it does not carry radiation reflected from or transmitted through the sample. It also includes the detector mentioned above for receiving the signal, if any, transmitted by the fiber-optic transmitter channel, and means for disabling the output in response to a signal coming from the transmitter channel. The result is that the system is disabled when a signal above a baseline level is transmitted along the fiber-optic channel to the detector, as a result of exposure to ambient light, as, for example, when a cuvette or sample holder is disconnected from the instrument.

The sensor in which such a disabling system is incorporated includes a radiation source, a detector for receiving a reflected or transmitted signal from the sample, a radiation-carrying channel extending from the source to the sample, a second transmitting channel extending from the sample to the detector, and a means for providing output based on the received signal It is usually a fiber-optic oximeter for measuring oxygen saturation or hematocrit in the blood.

Preferably, in this aspect of the invention, all transmitter and radiation carrying channels are fiber-optic channels, the second transmitter channel runs parallel to the first and all channels are insulated along their length from undue ambient light.

The preferred system also includes means for determining when the signal from the isolated transmitter exceeds background noise and sensor output is disabled only when that signal exceeds background noise. In general, the sample is a fluid, usually blood, passing through a cuvette attached to the radiation-carrying and transmitter channels.

As mentioned above, the device in which the system is incorporated is preferably an oximeter for measuring oxy- and deoxyhemoglobin, where the radiation source emits radiation at a wavelength at which oxy- and deoxyhemoglobin show substantial differences in absorption. The device usually includes a second radiation source emitting radiation at about the isobestic point for oxy- and deoxyhemoglobin.

In another aspect, the invention is a fiber-optic sensor for measuring components of a composition by detecting transmitted or reflected, usually reflected, radiation. The sensor includes a holder for the composition, a radiation generator, a first fiber-optic channel extending from the generator to the holder for carrying the generated radiation to the composition, a second fiber-optic channel extending from the holder to a detector for transmitting radiation from the composition to the detector, the detector itself, means for calculating the amount of a component in the sample composition based on the amount of transmitted radiation, and an output means for providing the calculated amount to the user.

The sensor also includes a third fiber-optic channel extending from the holder to a detector, a means for isolating the third fiber-optic channel from generated and transmitted or reflected radiation, and a detector for reading the signal from the third fiber-optic channel Finally, a means for disabling the device in response to the signal from the third fiber-optic channel is included so that if ambient radiation enters the system such as when the holder is disconnected from the fiber-optic channels, the device does not provide erroneous readings.

Preferably, all fiber-optic channels are insulated from ambient radiation, and the sample holder is a cuvette having an absorptive portion adjacent the third fiber-optic channel, to prevent reflected (or transmitted) radiation from the sample from being transmitted along the third fiber-optic channel Usually, the composition is blood, the radiation generating means are LEDs and the composition components being measured are oxy- and deoxyhemoglobin. Preferably, the disabling means is in the form of software.

In yet another aspect, the invention is a method of disabling the output of an oximetric device when the fiber-optic channels are exposed to undue ambient radiation as when a sample holder is disconnected from the device. It includes the steps of providing a radiation-carrying channel extending from a terminus adjacent the sample to a detector, isolating the channel from the sample and from ambient radiation, detecting radiation carried by the channel, and disabling the output of the device in response to radiation detected from the channel Usually, it also includes the step of determining when the radiation exceeds background noise, and the step of disabling comprises disabling the output of the device when the radiation exceeds background noise Preferably, the step of isolating involves providing a radiation-absorbing area adjacent the sample at the terminus of the channel. Preferably, a radiation source in the form of an LED is provided, as is a fiber-optic channel extending from the source to the sample, a detector for receiving the reflected or transmitted radiation, usually reflected, from the sample, and a means for providing output calculated from the amount of detected radiation to the user, the output representing a property of the sample. Usually, the radiation-carrying channel is provided parallel to the fiber-optic channel, and the step of isolating includes isolating both channels from substantially all ambient radiation. More preferably, the step of isolating includes providing a sample holder and providing a radiation-absorbing area on the holder adjacent the terminus of the radiation-carrying channel to preclude the radiation-carrying channel from carrying radiation reflected from or transmitted through the sample.

In another aspect, the invention is a cuvette for use in the above sensor or system.

BRIEF DESCRIPTION OF THE DRAWINGS

FIG. 5A is a cross-section of the lock or latch mechanism attaching the cuvette to the main cable; FIGS. 5B and 5C are enlargements of same.

DETAILED DESCRIPTION OF THE SPECIFIC EMBODIMENT

The disconnect detector system is part of a fiber-optic sensor system as described below.

I. Overall Fiber-optic Sensor System

Figure 1:
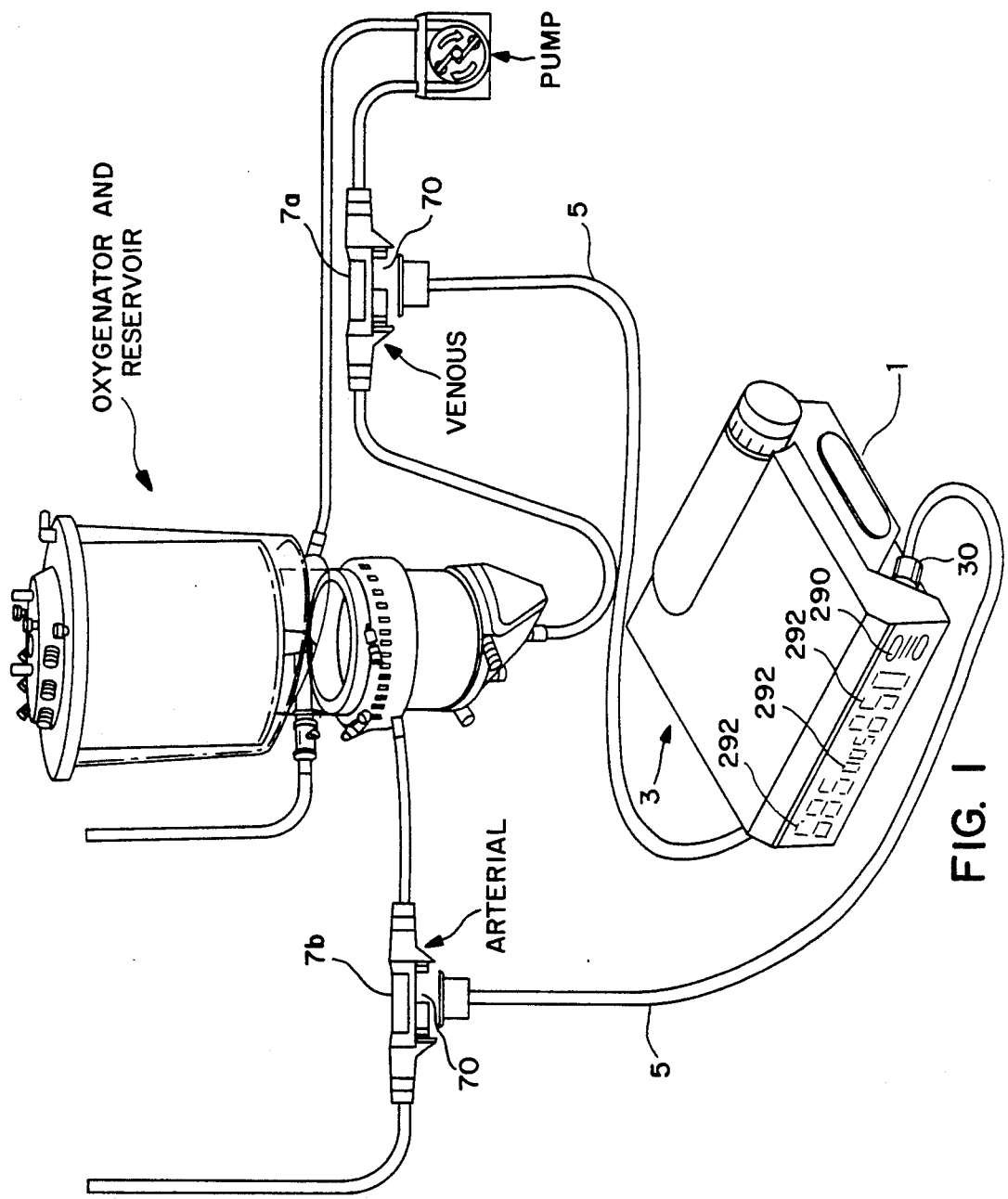
FIG. 1 is an overall illustration of the entire system.

The preferred embodiment of the system 1 shown in FIG. 1 includes an instrument or electronic module 3 housing LEDs, photodetectors, and hardware and software. Two non-disposable fiber-optic cables 5 and two cuvettes 7a and 7b which are placed in the blood stream path are included so that oxygen saturation and hematocrit in blood passing through the cuvettes in the extracorporeal blood circuit can be measured. A printer (not shown) can be attached to the module or housing 3. One cuvette 7a is located in the venous flow path and one, 7b, is located in the arterial flow path, so oxygen saturation and hematocrit of both can be monitored and displayed. The device is physically and operationally identical for both the arterial and venous paths, except where indicated below; therefore only one of the two paths is described below unless specific description of the other path is necessary.

II. Fiber-optic Cable

Figure 2A:
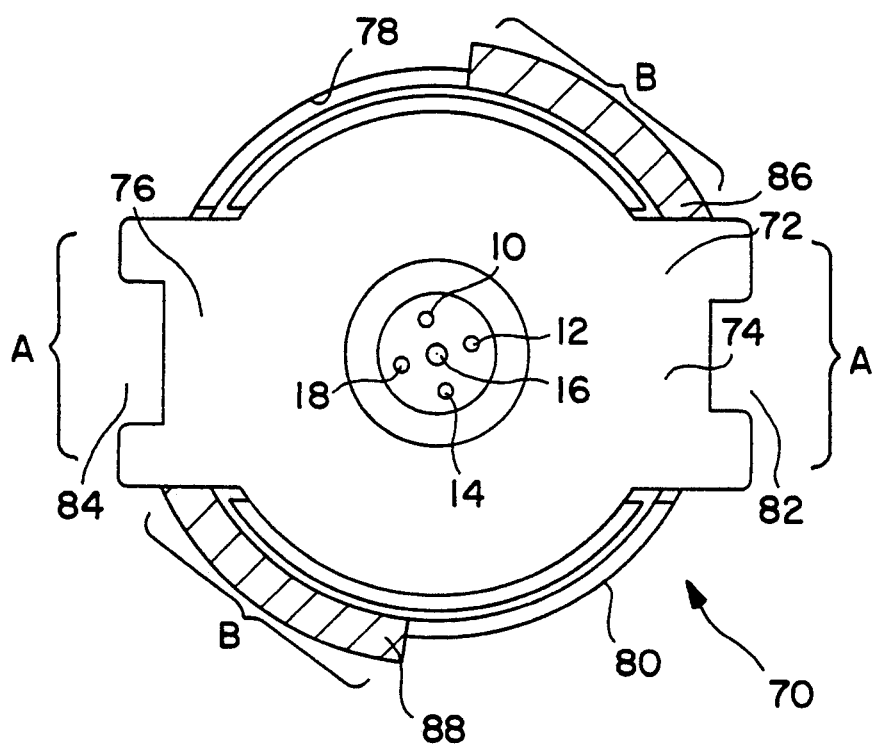
FIG. 2A is a plan view of the end of the fiber-optic cable where it attaches to the cuvette.
Figure 2B:
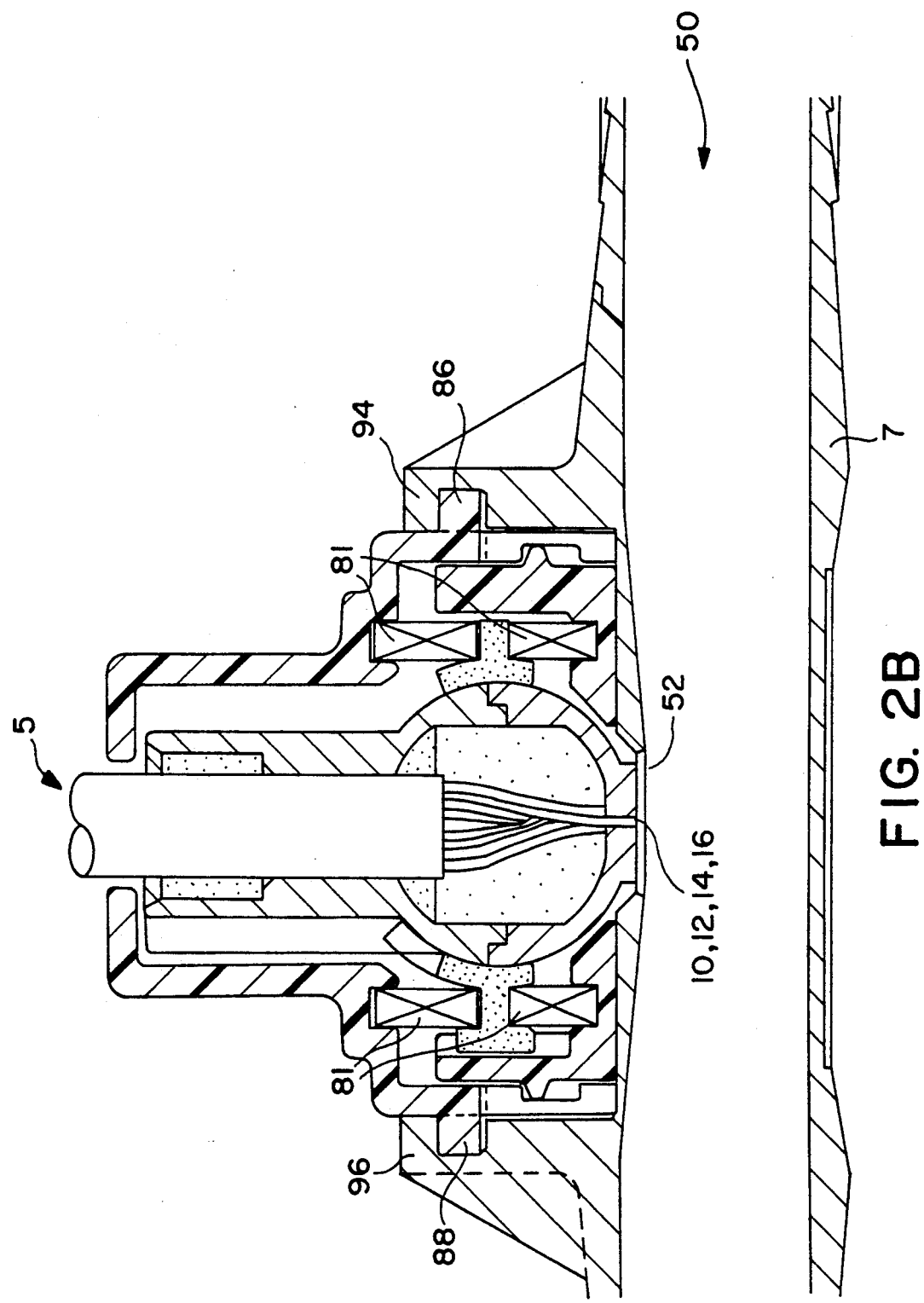
FIG. 2B is a longitudinal cross-section of the cuvette attached to the cable.

Referring to FIGS. 2A and 2B, the preferred cable 5 includes five fiber-optic channels. The fiber-optic channels are formed of polymethyl methacrylate with a fluorinated polymer cladding. One is an emitter channel 10 for transmitting 660 nm radiation from a 660 nm LED (20 in FIG. 6A) to the blood sample; a second is an emitter channel 12 transmitting 810 nm infrared radiation from an 810 nm LED (22 in FIG. 6A) in module 3, to the blood sample; a third is an emitter channel 14 transmitting 830 nm IR radiation from an 830 nm LED 24 in module 3 to the blood sample. A single LED at the true isobestic wavelength and corresponding channel can be chosen, if available, to avoid the need for both the 810 and 830 nm channels. These emitter channels transmit the radiation through the window of the cuvette 7, discussed below, to the blood sample, illuminating the blood.

The fiber-optic cable 5 also includes fourth channel 16 for receiving reflected radiation at the input wavelengths, and transmitting it to a signal photodetector 258 (shown in FIG. 6A) in the electronic module. This preferred embodiment measures reflected light, as indicated, but it is within the scope of the invention to measure transmitted light as well.

At the distal end of the cable, the fiber-optic channels are spaced with the emitter channels equidistant from detector channel 16, as shown in FIG. 2A. The preferred fiber-optic channel size for all the emitter channels is 0.030 inches in diameter, the detector channel is preferably 0.040 inches in diameter and all emitter channels are preferably located about 0.047 inches from detector channel 16. For a particular device, the distance of the emitter channels from the detector channel at the blood interface can be optimized using methods known in the art.

Disconnect detector channel 18 for connection with disconnect photodetector 262 in module 3 is also included in cable 5, preferably located at the same distance from the detector channel as the emitter channels at the blood interface end of the cable.

III. Bulkhead Connector

Figure 3A:
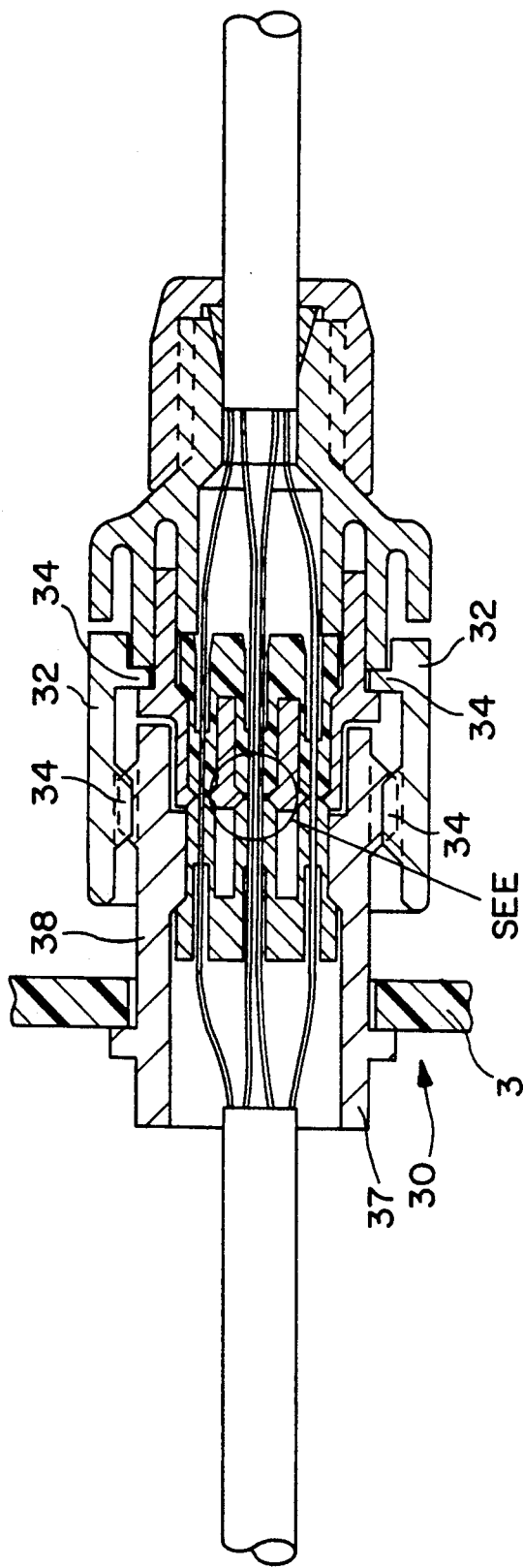
FIG. 3A is a cross section of the bulkhead connector between the cable and the instrument.

The proximal end of the cable is attached to instrument 3 via a bulkhead attachment 30 shown in cross-section in FIG. 1 and FIGS. 3A, and in 3B and 3C. A round female unit 32 having interior threads 34 and a key 36 is rotatable with respect to the cable. A male unit 38 with threads 31, mounting unit 37 for mounting in housing 3, and key slot 35 is disposed in module 3.

Figure 3B:
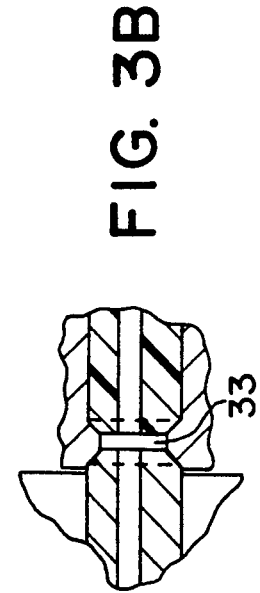
FIG. 3B is an enlargement of the area where the fiber-optic channels connect.
Figure 3C:
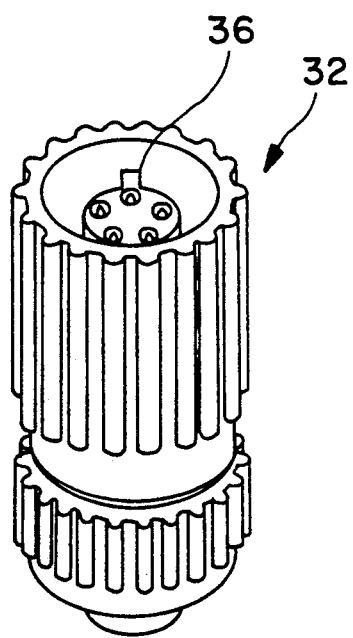
FIGS. 3C and 3D are isometric end views of the two parts of the bulkhead connection.
Figure 3D:
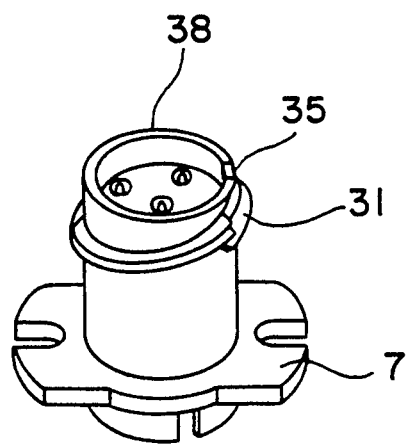

To connect the cable to the module, the male unit is placed within the female unit, key slot to key, and the female unit 32 is rotated to attach the cables to the bulkhead, companion fiber-optic channels not more than 0.010 inches apart from each other. An enlargement of the connection is shown in FIG. 3B, with a small space 33 of not more than about 0.010 inches between the companion channels.

IV. Cuvette

A cuvette 7a or 7b shown in FIGS. 2B, 4A, 4B, and 4C is placed within the extracorporeal blood path for blood flow therethrough during bypass surgery. The blood flows longitudinally through the cuvette through axial cavity 50. The cuvette is molded of polycarbonate for convenient light transmission, and is of generally cylindrical shape. Barbed fittings 51 at each end are designed to fit within the tubing of the extracorporeal circuit with a leak-free seal. Window 52 includes an absorptive well 54 (usually painted with black epoxy) located immediately opposite disconnect detector channel 18.

In use, second or disconnect detector channel 18 abuts well 54 in cuvette 7. Because well 54 is covered with a light-absorbing material such as black epoxy, disconnect detector channel 18 transmits no light to its photodetector when the system is properly operating. When light is transmitted to the disconnect photodetector 258 (shown on FIG. 6A), indicating the presence of ambient light in the system, an error message is displayed and the system must be checked for correct hookups, breaks, and the like, and if breaks have occurred, replacement parts must be used and calibrated.

V. Latch Connector

When in use, the cuvette is attached to the cable via lock or latch 70 shown in FIGS. 1, 2A, 4A, and 5A through 5D. On cable 5, the lock includes knob 72 rotatable with respect to foot 73 containing the fiber-optic channels. Foot 73 has stops 74 and 76 which limit rotation of knob 72 when they contact extensions 78 and 80. Springs 81 bias foot 73 away from cable 5. Stops 74 and 76 contain key slots or channels 82 and 84, preferably of different sizes. Extensions 78 and 80 together with stops 74 and 76 define an area of rotation of knob 72; the knob can be rotated so that the key slots are located at a position A or a position B as shown. Adjacent the key slots when they are located in position B are lips 86 and 88, each with its own stop 90 and raised lock 92.

Cuvette 7 contains keys 94 and 96, each designed to be received in one of slots 82 or 84; space 95 between them is designed to receive foot 72. Each key defines an aperture 98 and flange 97 which can receive a lip 86 or 88.

The cuvette is attached to the cable by sliding the keys into the appropriate key slots when knob 72 is in position A. Cuvette 7 and foot 73 are then urged toward the cable and the knob rotated so that cuvette flanges 97 pass over locks 92 and reach stops 90 with the knob in position B. Pressure on the cuvette and foot is then released and spring 81 in cooperation with locks 92 firmly hold the channel and cuvette in place with channels 10, 12, 14, 16 abutting window 52 of the cuvette.

VI. System Block Diagram

Figure 6A:
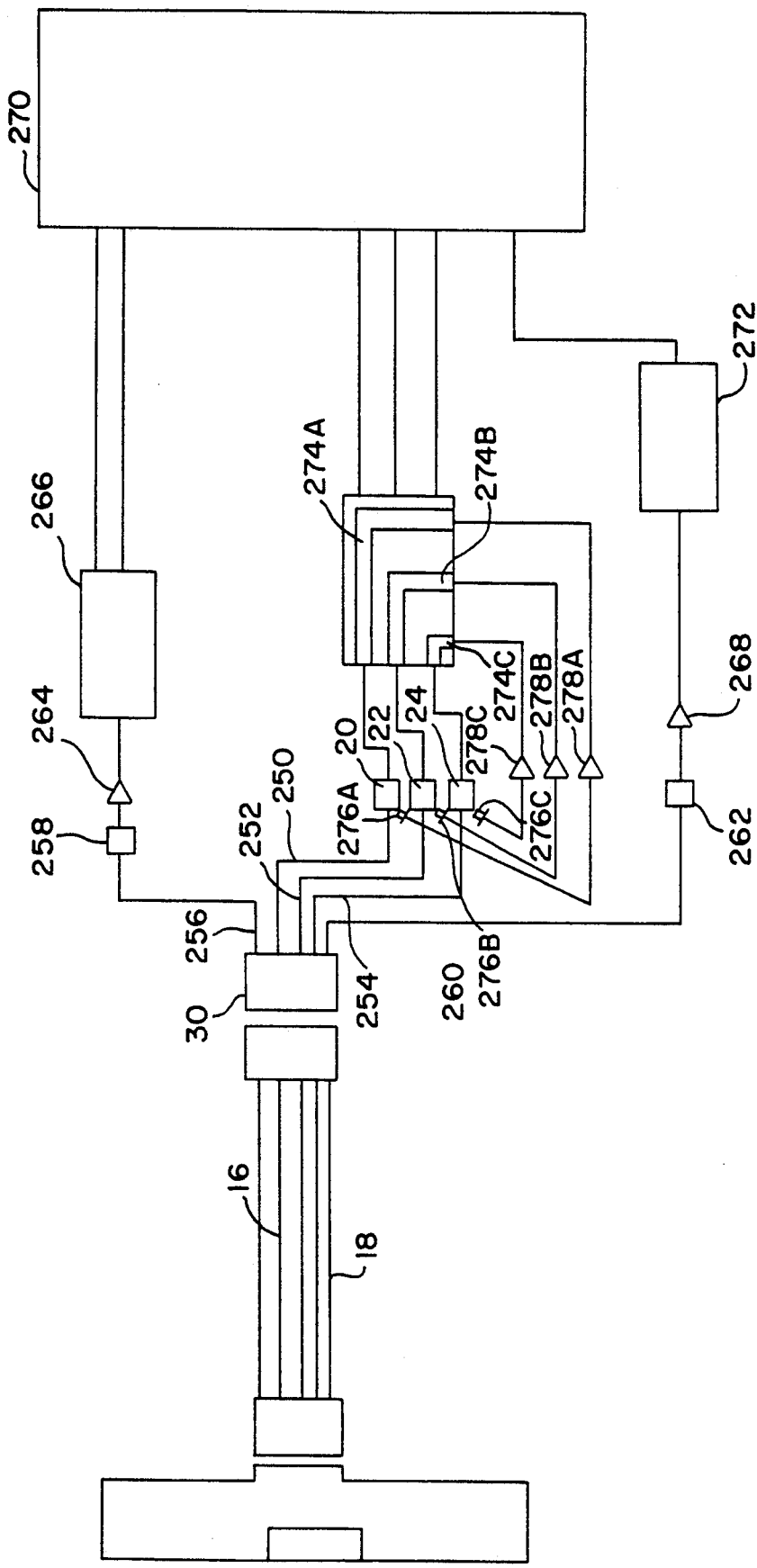
FIGS. 6A and 6B form a system block diagram for the device.
Figure 6B:
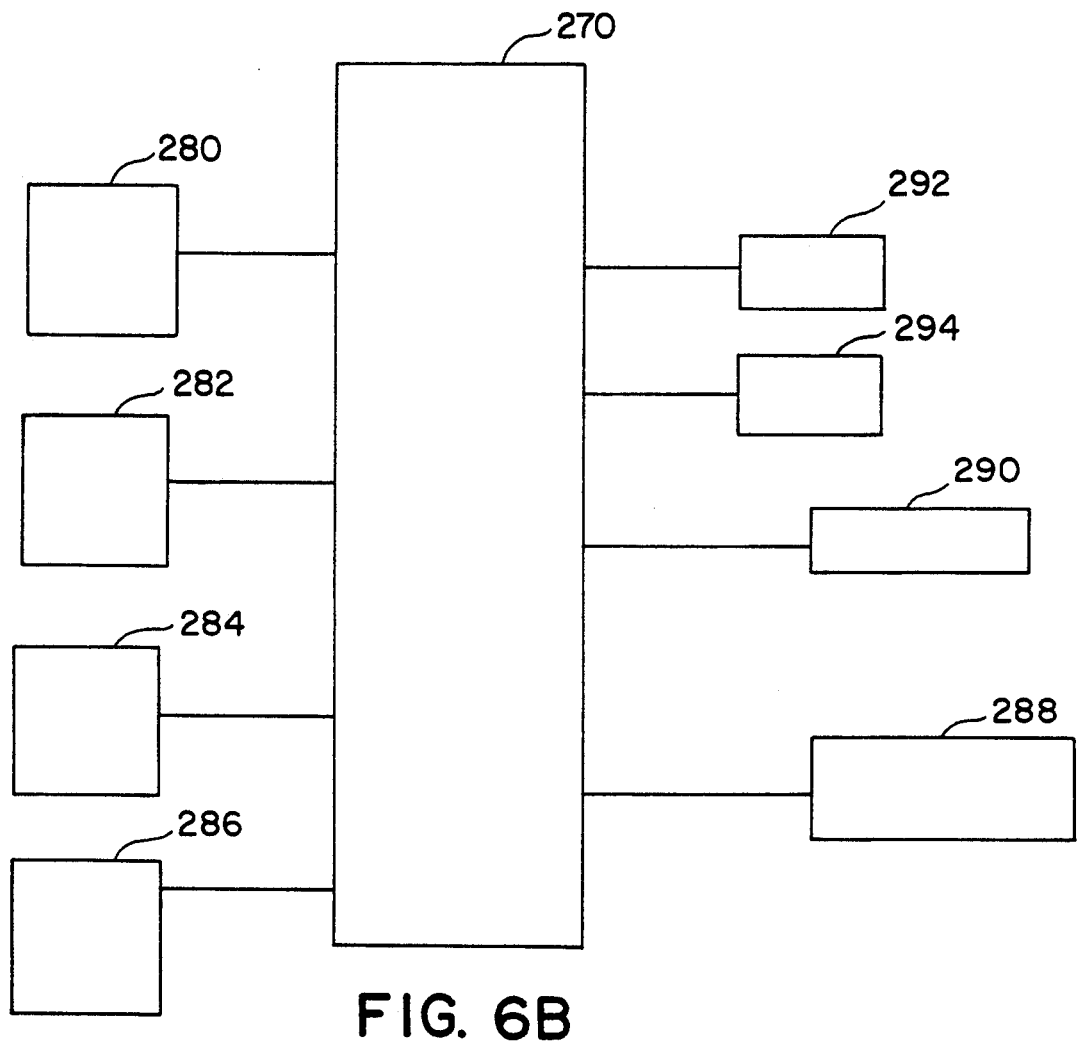

A system block diagram for the entire device is shown in FIGS. 6A and 6B. Bulkhead connector 30 contains three optical channels 250, 252, and 254 to conduct LED illumination through the bulkhead. It also contains on optical channel 256 to conduct reflected signal energy to the signal detector 258 and one optical channel 260 to conduct disconnect signal energy to the disconnect detector 262.

Signal detector 258 is connected to the signal detector amplifier 64 that amplifies the signal in a range usable for the analog-to-digital converter 266 The analog-to-digital converter data is fed to the CPU 270.

Figure 8:
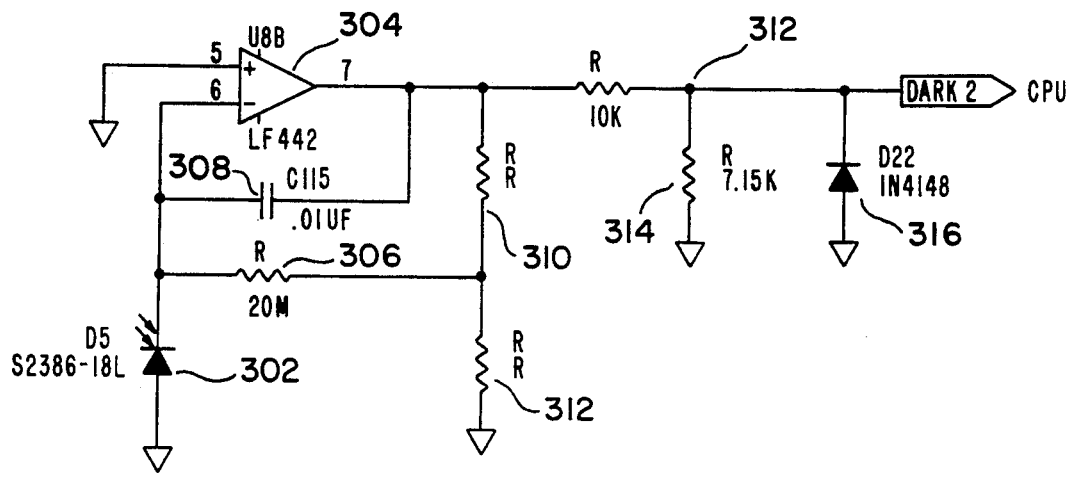
FIG. 8 illustrates the circuit employed in the present invention in connection with the disconnect detector.

Disconnect detector 262 is connected to the disconnect detector amplifier 268 which amplifies the disconnect signal to a range usable by analog-to-digital converter 272. The converter data is interpreted by the CPU. Referring specifically to FIG. 8, the disconnect detector circuit 300 includes a photodiode 302 producing current which is fed to op amp 304. Op amp 304, resistor 306 and capacitor 308 form a transimpedance amplifier with voltage gain resulting from connection to resistors 310 and 312. Junction 312 connected to resistor 314 and ground forms a voltage divider as a safety mechanism to limit the amount of current passed to CPU 270. Diode 316 to ground is a safety mechanism preventing a short circuit from feeding into the CPU. Optical channels 250, 252, and 254 are coupled to individual LEDs 20, 22 and 34 of the three wavelengths 660 nm, 810 nm, and 830 nm, respectively. Each LED is energized by its LED driver, shown as one of 274a, b, or c on FIG. 6A. Each LED driver is individually turned on and off by the CPU. The intensity of each LED is controlled by an individual compensation circuit. Each compensation circuit consists of a compensator detector, one of 276a, b, or c to monitor the LED energy. Each compensator detector is coupled to a compensator detector amplifier, one of 278a, b, or c, which amplifies the signal. Each compensator detector amplifier signal is coupled via a multiplexer, a comparator-integrator and another multiplexer to the appropriate LED driver 274a, b, or c. If the LED energy varies from its set point, this information is fed to the LED driver and the LED driver adjusts the LED energy as necessary to maintain the set point.

In operation, individual LED energies are sequentially triggered to illuminate the sample via cable 5. The reflected energy from the sample is transmitted through the detector channel 16 in cable 5 to the signal detector 258. The signal is amplified by the signal detector amplifier 264, converted to digital data via the analog digital converter 266, and read by CPU 270. Preferably, the individual LEDs are triggered so that the detector reads first the "ambient" light received along the channel and then reads the reflected light at the LED wavelength received along the same channel. The "ambient" data is subtracted from the reflected data in the software before correction for calibration.

Referring now to FIG. 6B, the CPU 270 is a standard 8-bit microcontroller with RAM 280, ROM 282, a watch dog timer 284, and an asynchronous serial port 286 for attachment to printer 2 in this case. Additional system components are the power supply 288, an LCD display 290, a test switch 292 and an event switch 294 all connected to the CPU.

VIII. Software

A. Calibration

When the device is first used, it is calibrated to compensate for variations in the individual system's optical components; by taking measurements under known conditions, normalization factors can be determined for each LED emitter channel and detector channel combinations. Such factors are developed to correct the raw readings at each channel for variations inherent in each system.

Figure 4A:
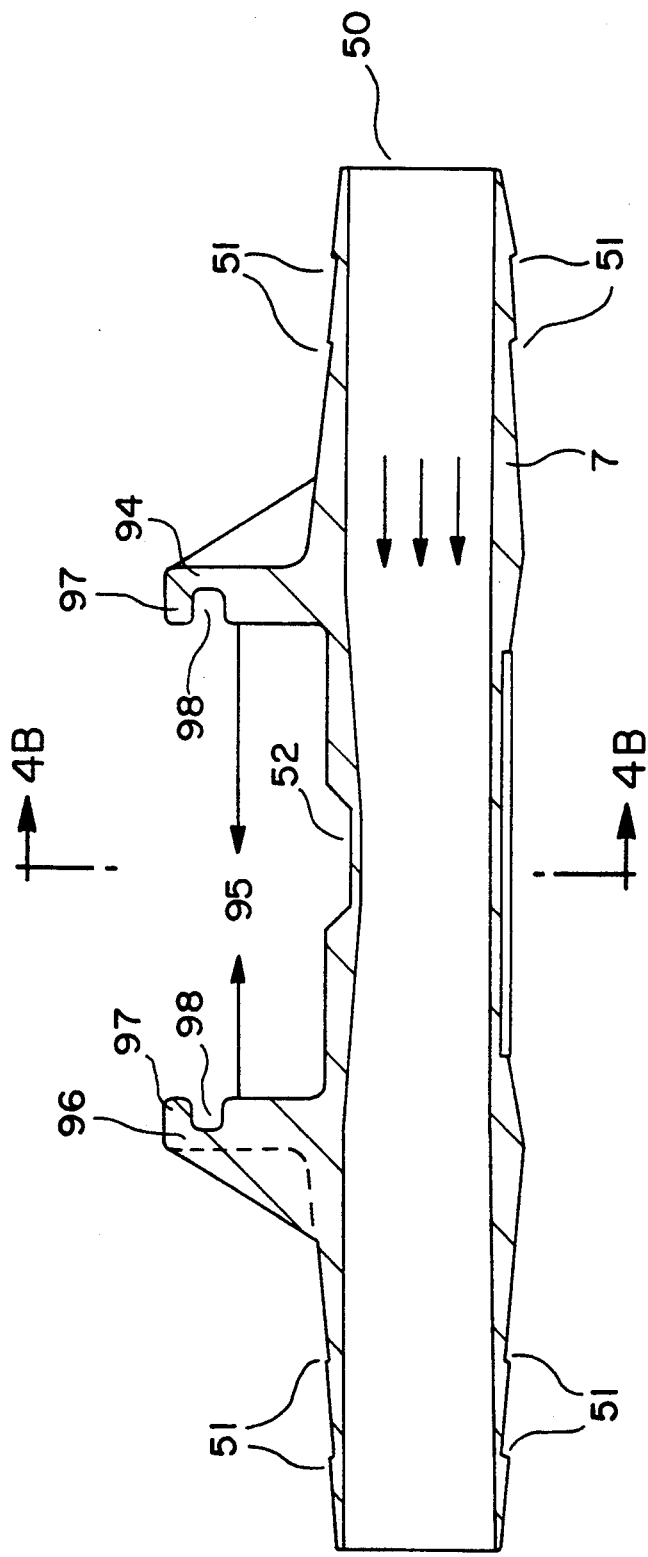
FIG. 4A is a longitudinal cross-section of the cuvette.
Figure 4B:
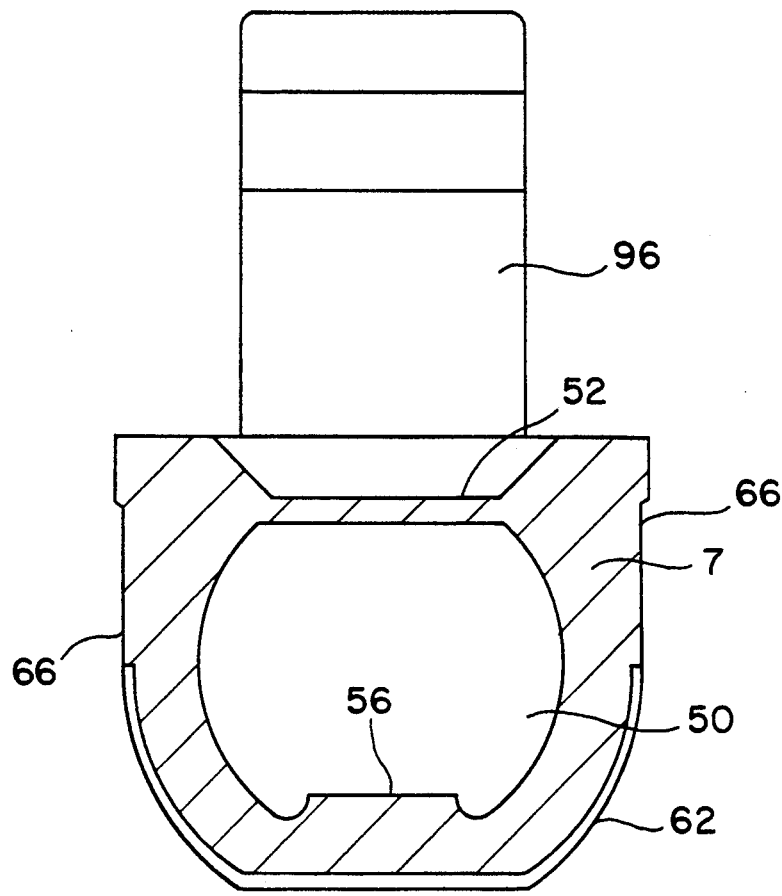
FIG. 4B is a cross-section of the cuvette taken at lines 4B—4B of FIG. 4A.
Figure 4C:
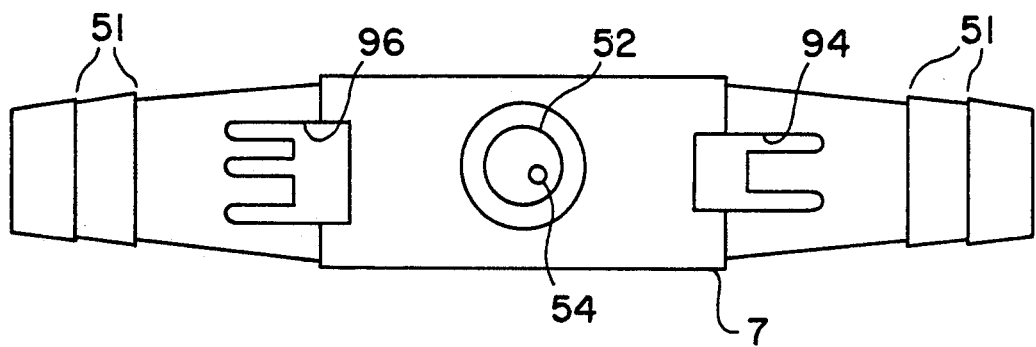
FIG. 4C is a top view of the cuvette and window.
Figure 4D:
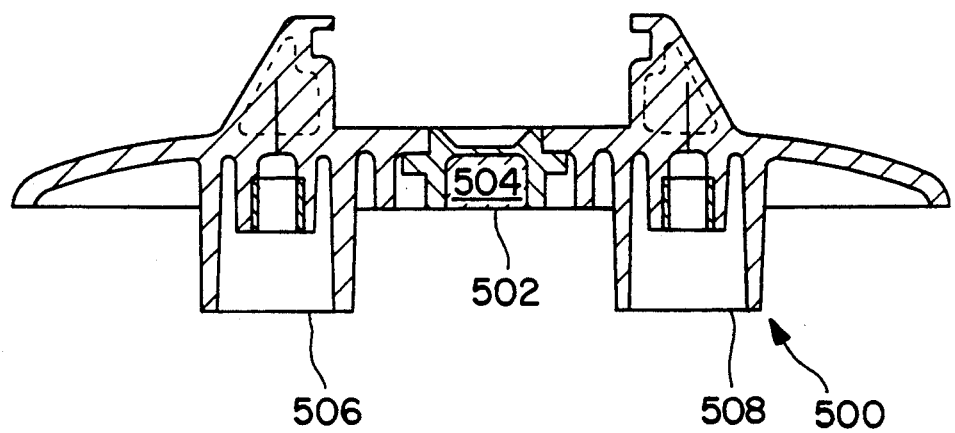
FIG. 4D is a longitudinal cross-section of the calibration cuvette for the system.
Figure 5D:
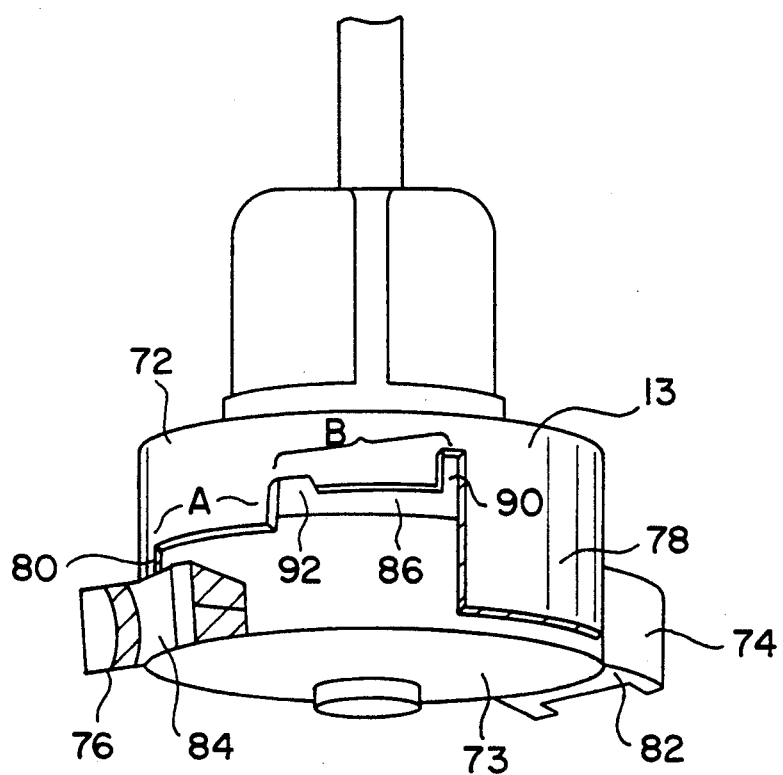
FIG. 5D is a side elevation of the latch mechanism.

Calibration is accomplished in the preferred embodiment using a calibration cuvette 500 shown in FIG. 4D. This is a cuvette designed to be attached to the cable unit in the same fashion as a standard cuvette. However, it contains a material designed to provide a known amount of reflected light in the device at the selected wavelengths.

The calibration cuvette does not contain a chamber for blood passage; instead, it contains a well 502 to contain reflective material 504. Preferably, for simplicity of manufacture, it otherwise duplicates the standard cuvette as much as possible. Also, it terminates in two bases 506 and 508 which are permanently adhesively attached to the instrument module 3 for convenience of use for each calibration. Material 504 is designed to resemble blood in that the amount of light reflected is similar to that of blood. Since the preferred device is designed to operate maximally with blood giving a signal of about 2.0 to 3.0 volts, the preferred calibration standard gives a signal in this range also.

In an attempt to maximize accuracy of the calibration, the device is preferably calibrated using a calibration standard (material 504) providing a voltage just above the maximum reflected voltage level for blood. Using as high a voltage as possible within the desired level minimizes the effect of errors in the calibration reading on the normalization factors which calibration creates. The maximum voltage read from blood in the preferred embodiment at the 660 nm wavelength is about 2.8 volts while the maximum at the 810 and 830 nm wavelengths is about 2.5 volts. In the preferred embodiment, thus, the calibration standard reflects at a level equivalent to 3.0 volts on the 660 nm channel and 2.5 volts on the 810 and 830 nm channels.

The material used for the calibration includes a light-scattering agent dispersed at desired levels in a support medium. The support matrix is substantially non-light-absorbing at the wavelengths of interest and may be formed of a number of materials such as silicone elastomers (like Dow Corning's Silastic MDX 4-4210), urethanes, epoxy, or other materials. The support matrix is generally chosen for certain characteristics. Specifically, it should cure to a solid fairly quickly without allowing the dispersed materials to settle out. Once cured, its viscosity and other features should be stable over time. The preferred support matrix is epoxy which shows limited degradation over time.

A number of light-scattering materials can be used such as titanium dioxide, Tempera paint pigment, silicon carbide, ferric oxide, etc., which can be evenly dispersed in the matrix. These materials should be generally non-varying over time and, if possible, of a uniform particle size.

In some embodiments, dyes may be used to diminish the reflected light at certain wavelengths. These dyes may be included in the support matrix or may be independently dispersed. Some possible dyes are PSP030, a blue pigment dispersion made by Huls Petrarch, Inc., or Thymol blue made by Fisher Chemical Company. The blue dyes will reduce the amount of reflected red light.

The preferred material, specifically, will include about:

59.4% by weight: Epoxy resin
35.6% by weight: Epoxy hardener
5.0% by weight: Titanium dioxide powder The preferred epoxy is Hexcel Epolite 3310, a 75 Shore D clear epoxy.

The preferred titanium dioxide (or Titanium (IV) Oxide) is a white powder of greater than 99.9% purity in the anatase form.

The mixture is cured in the cavity 502 of calibration cuvette 500 shown in FIG. 4D and is preferably about ¼ inch thick, or at least thick enough and sufficiently opaque so that ambient light does not enter from the rear.

The calibration constants in the preferred device, 3.0 volts for the 660 nm channel, 2.5 volts on the 810 channel, and 2.5 volts on the 830 nm channel are used to calculate normalization factors as follows:

$$\text{Normalization factor} = \frac{\text{Constant for wavelength}}{\text{Reflected light at wavelength during calibration}}$$

For example, if the voltage read on the 660 channel using the standard is 2.9, the normalization factor for that channel is:

$$\text{Normalization factor} = \frac{\text{Constant}_{660}}{\text{Voltage}} = \frac{3.0}{2.9} = 1.03$$

If, for example, on the other two channels, the voltage on the nm channel during calibration is 2.4 and that on the 830 channel is 2.3, the normalization factor for each will be:

$$\text{Normalization factor}_{810} = \frac{\text{Constant}_{810}}{\text{Voltage}} = \frac{2.5}{2.4} = 1.04$$

and $$\text{Normalization factor}_{830} = \frac{\text{Constant}_{830}}{\text{Voltage}} = \frac{2.5}{2.3} = 1.09$$

These factors are stored in RAM as the normalization factors for each channel, and thus readings on each channel are separately calibrated and corrected for variability of the system.

Figure 7A:
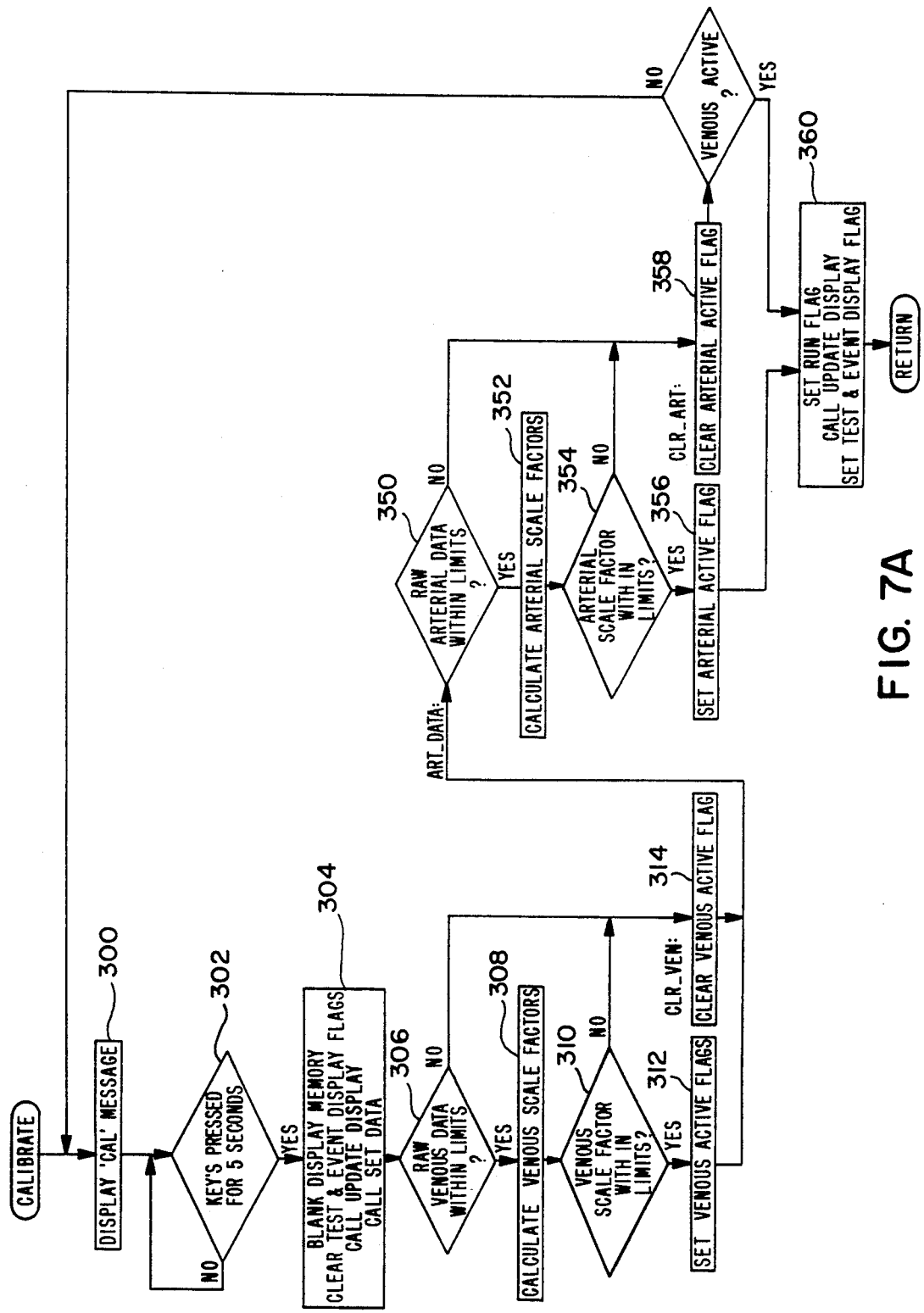
FIGS. 7A and 7B are flow charts, respectively, of the software for the "Calibrate"mode and the "Run" mode.

A software flow diagram for the calibration process is shown in FIG. 7A.

The CPU first displays "Cal" in the arterial and venous windows 292 to prompt the operator to depress the Test switch 290, and waits for the switch to be held for at least 3 seconds, steps 300, 302 in FIG. 7A. The LED drivers are then directed to energize the LEDs sequentially, step 304.

Data is acquired on the venous and arterial channels at each wavelength as follows. Detector voltages are captured for each wavelength on the venous channel in the hardware capture circuitry described previously. Each captured venous voltage is digitized and stored in RAM in the venous data table, step 304. The same steps are taken for the arterial channel, step 350.

Normalization factors are calculated for each wavelength by the CPU using the acquired data, steps 308, 352. Raw data and the normalization factors are then compared to preset limits for validation, steps 306, 310, 350, 354. If either channel is found to be invalid, the CPU blanks the display. If both channels are invalid, a "Fail" flag is set (and displayed), the "Cal" flag is redisplayed and the procedure must be restarted, steps 314, 358, or problems with the device corrected.

If the venous channel data and normalization factor are found to be valid, an active channel flag is set; the same is done for the arterial channel, step 356. A "Pass" flag is then set and displayed, step 360. If one of the channels is invalid, its display window is blanked.

In use, the CPU uses the normalization factors for each channel to correct raw readings before calculating hematocrit and oxygen saturation via software contained in RAM.

B. Run Mode

Figure 7B:
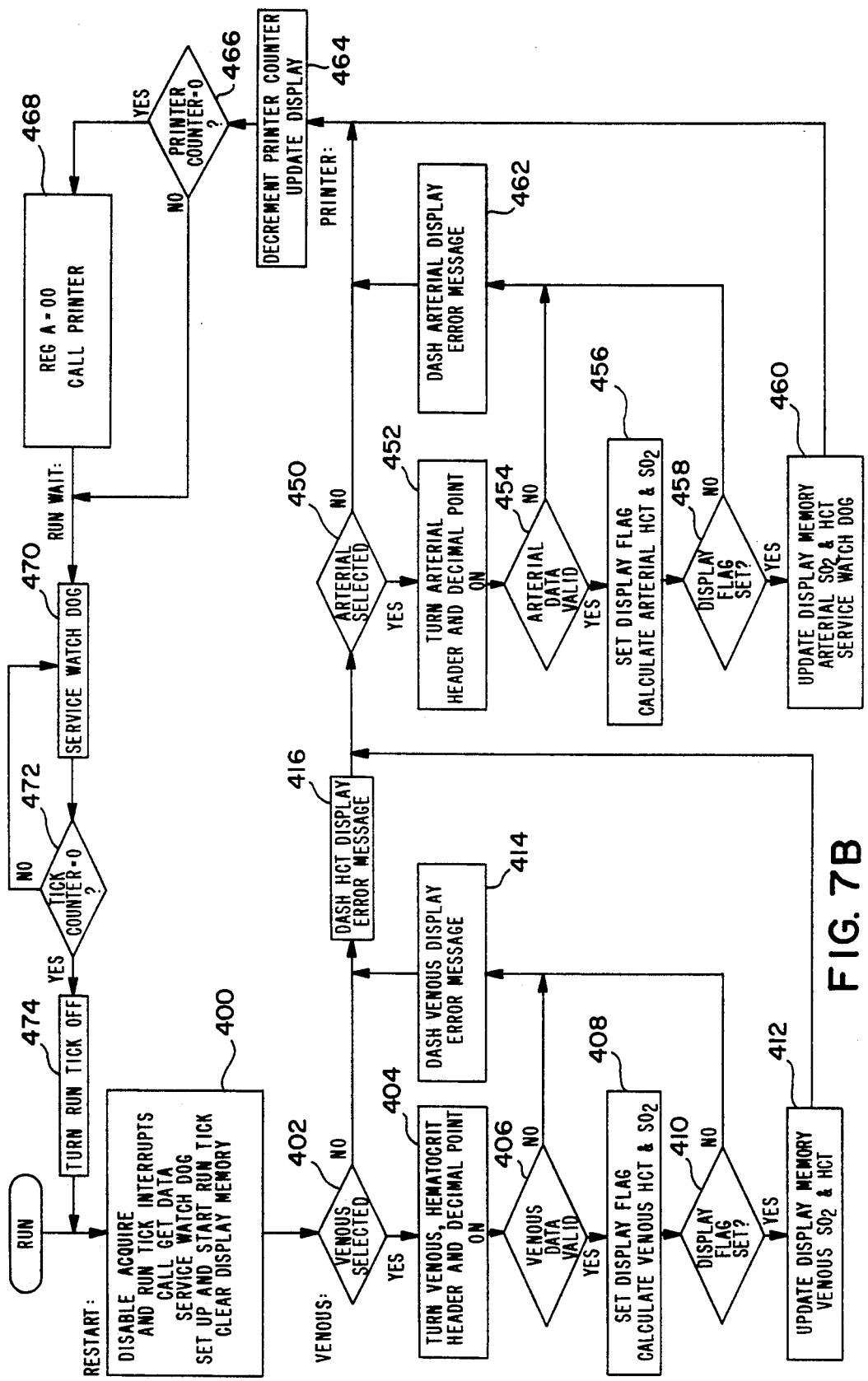

After calibration, the device operates in the "Run" mode. All variables, flags and registers are initialized for the run mode and normalization factors are included. The run mode is the normal operational mode for the instrument that is active until the device is powered down. An itemization of one run mode cycle after initial testing (step 400, as described above) is then shown in FIG. 7B.

The detector voltages are captured and processed as described in the calibration section above, steps 402, 404, 450, 452. The output is the venous data table which contains values for each wavelength and the arterial data table, which also contains output for each wavelength.

The venous data is processed as follows. If the venous channel is not active, the procedure is exited, 402, and arterial procedure entered. If active, the venous channel data is compared to acceptable limits, 406. If the venous data is not valid, an error message is displayed in the venous display window, 414, and the procedure is exited. If valid, the data (which has already been corrected for ambient signals) is adjusted for VCO non-linearieties.

Finally, the data for each channel is then normalized, using the normalization factors obtained in the calibration mode. This is done by multiplying the received data by the multiplicative scale factor determined during calibration. For example, in the example shown, the received data on the 660 channel will be multiplied by 1.03, on the 810 channel by 1.04, and on the 830 channel by 1.09. Calculation of hematocrit and then oxygen saturation is then completed as described later using the normalized data.

Venous saturation results produced as described above are then displayed, 410, 412. Arterial channel data is similarly processed, steps 462–462, but venous hematocrit is displayed, 416, if the channel is inactive. Otherwise, arterial saturation and hematocrit are displayed, 460. A printer can be used if desired, see 464–468.

The disconnect system prevents continued operation if a disconnect is detected while the device is in "Run" mode. Specifically, if the entire system is intact, the disconnect signal is a near-zero set-point (preferably about 50 mv). If the cuvette (or cable) is disconnected (or broken), the disconnect signal will include ambient signal energy or LED signal energy reflected from any nearby surface. If a disconnect signal greater than the set point is received by the CPU, it delivers an error message to the display.

VIII. DETERMINATION OF HEMATOCRIT AND OXYGEN SATURATION

A. Hematocrit

Where an LED is used which actually produces a wavelength at the isobestic point (about 820 nm) for hemoglobin and deoxyhemoglobin, that measurement is used for hematocrit. Specifically, using the normalized data, a reflectance measurement is obtained, as follows:

$$R_H = R_{ISOBESTIC}$$

Figure 9:
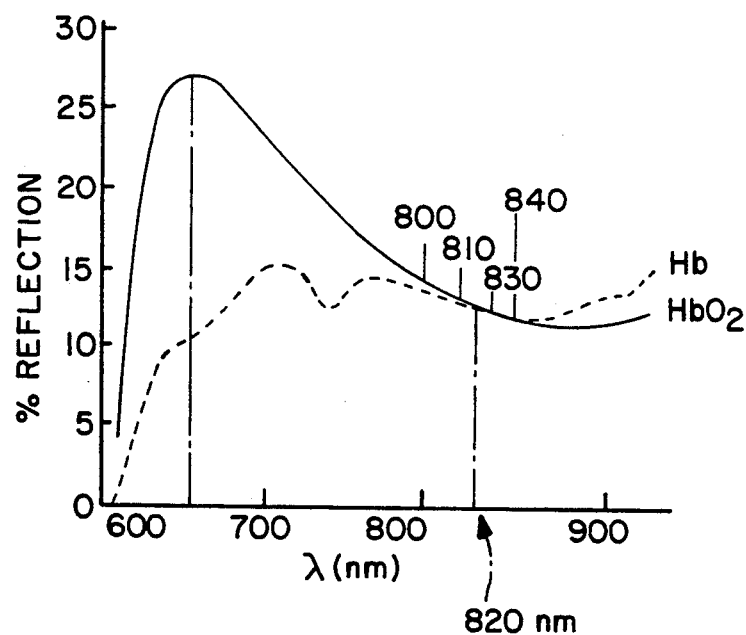
FIG. 9 is a graph of the reflection curves of deoxygenated and oxygenated hemoglobin showing the isobestic point.

In the preferred embodiment, LEDs generating wavelengths symmetrically disposed about the isobestic point on the oxy- deoxyhemoglobin curve are used. As can be seen on FIG. 9, if an LED generating the exact isobestic wavelength is not available for the device, two LEDs generating wavelengths disposed on either side of the isobestic point can be used. The difference between the two curves at the one wavelength should be equal but opposite to the difference between the two curves at the other wavelength.

In the present case, LEDs generating wavelengths of 810 nm and 830 nm are used. Thus, $R_H$ can be calculated as follows:

$$R_H = \frac{R_{810} + R_{830}}{2} \text{ or } R_{810} \times R_{830}$$

Hematocrit (Hct) can then be calculated as follows using the $R_H$ value:

$$\% \ Hct = A \cdot R_H + B \cdot (R_H^2) + C/R_H + D/(R_H^2)$$

This equation, including constants A, B, C, D, was in this case empirically derived by comparing $R_H$ values and their associated known hematocrit values.

In the preferred embodiment, the constants are:
A = 19.670148
B = −6.833192
C = 9.833347
D = −0.86262

The above data has been found to provide error ranges of about ±3 units under normal physiological conditions.

B. Oxygen Saturation

Oxygen saturation is determined using a $Ratio_O$:

$$Ratio_O = \frac{R_{830}}{R_{660}}$$

Oxygen saturation is then calculated as follows, where Hct is the hematocrit value calculated above.

$$\% \ sO_2 = E \cdot Ratio_O + F/Ratio_O + G/(Ratio_O^2) + H \cdot Ratio_O/Hct + I \cdot Hct + J/Hct + K(Hct^2)$$

E through K are constants determined for the particular device before manufacture by comparing data from numerous devices to actual oxygen saturation figures.

Specifically, in the device shown,
E = 3.462727
F = 36.690131
G = −7.060379
H = −500.693864
I = 0.570215
J = 1425.89362
K = −7708.556902

This approach provides particularly accurate oxygen saturation data. The oxygen saturation data is corrected for hematocrit variations which are measured essentially instantaneously. Thus, variations in the hematocrit level during a bypass procedure do not result in erroneous saturation readings.

IV. Use of the Device

The device is first assembled before use, the second cable unit attached to the instrument using the bulkhead attachment and the cuvettes placed in what will be the extracorporeal circuit after it is primed. The cables are attached to the cuvettes using the latches. The device is calibrated using the calibration cells provided before connection to the cuvette.

Once the system has been primed and is running, the device can be used to measure hematocrit and oxygen saturation. Using the equations set forth above, the device displays hematocrit readings and oxygen saturation readings.

Due to the disconnect system, should the device become disconnected from the cuvette, or ambient light otherwise enter the system, the display is simply blanked out due to input from the disconnect detector channel, so erroneous readings are avoided. A printer can be activated to print readings if desired. Once the surgery is completed, the cuvette is removed from the circuit and disposed of, and the device readied for another use, with another cuvette, following the procedures described above.

It will be understood that the above description and the illustrations are provided by way of example only, that alternate versions, equivalents, and examples will be apparent to those skilled in the art, and will be within the scope of the invention which is defined by the appended claims. For example, transmitted rather than reflected light can be measured in certain instances with certain devices.

What is claimed is:

1. A device for measuring a feature of a sample, including a radiation source, a detector for receiving transmitted radiation, means for carrying radiation from the source to the sample, first means for transmitting radiation from the sample to the detector, means for providing output based on the received radiation, and further comprising:
    second means located adjacent the sample for transmitting radiation;
    means for isolating the second transmitting means from radiation from the sample; and
    means connected to receive radiation from the second transmitting means for disabling the output of the device in response to radiation received from the second transmitting means.

2. A device according to claim 1 wherein the first and second transmitting means and the carrying means are fiber-optic channels and the second transmitting means is isolated from ambient light and runs parallel to the first transmitting means.

3. A device according to claim 2 further comprising means for calculating the radiation received by the disabling means, the disabling means being responsive to the calculating means such that the output of the device is disabled when background noise is exceeded.

4. A device according to claim 3 wherein the isolating means comprises an area of radiation absorption adjacent the second transmitting means to isolate it from radiation reflected from the sample.

5. A device according to claim 4 wherein the device is a sensor device for measuring oxy- and deoxyhemoglobin in blood, wherein the radiation source emits radiation at a wavelength at which oxy- and deoxyhemoglobin show substantial differences in absorption, and comprising a second radiation source emitting radiation at about the isobestic point for oxy- and deoxyhemoglobin.

6. A fiber-optic sensor for measuring components of a composition by detecting transmitted or reflected radiation, comprising:

means for holding the composition:

means for generating radiation;

first fiber-optic channel extending from the generating means to the holding means for carrying the generated radiation to a sample composition;

second fiber-optic channel extending from the holding means for transmitting radiation from the sample;

a first detector for receiving radiation transmitted by the second fiber optic channel from the sample;

means for calculating the amount of a component in the sample composition based on the amount of radiation received by the first detector;

output means for providing an indication of the calculated amount;

third fiber-optic channel extending from the holding means for transmitting radiation;

a second detector for receiving radiation transmitted by the third fiber optic channel;

means for isolating the third fiber optic channel from generated and transmitted radiation; and means for disabling the output means in response to radiation received by the second detector so that if ambient radiation enters the system, the device does not provide erroneous readings.

7. A fiber-optic sensor according to claim 6 including means for insulating all fiber-optic channels from ambient radiation.

8. A fiber-optic sensor according to claim 6 and wherein the holding means is a cuvette and the isolating means is an absorptive portion of the cuvette adjacent the third fiber-optic channel.

9. A sensor according to claim 6 wherein the means for generating radiation are LEDs.

* * * * *